June 3, 1952 J. G. SCHILT Plant Pat. 1,101
CHAMAELAUCIUM PLANT
Filed April 30, 1951
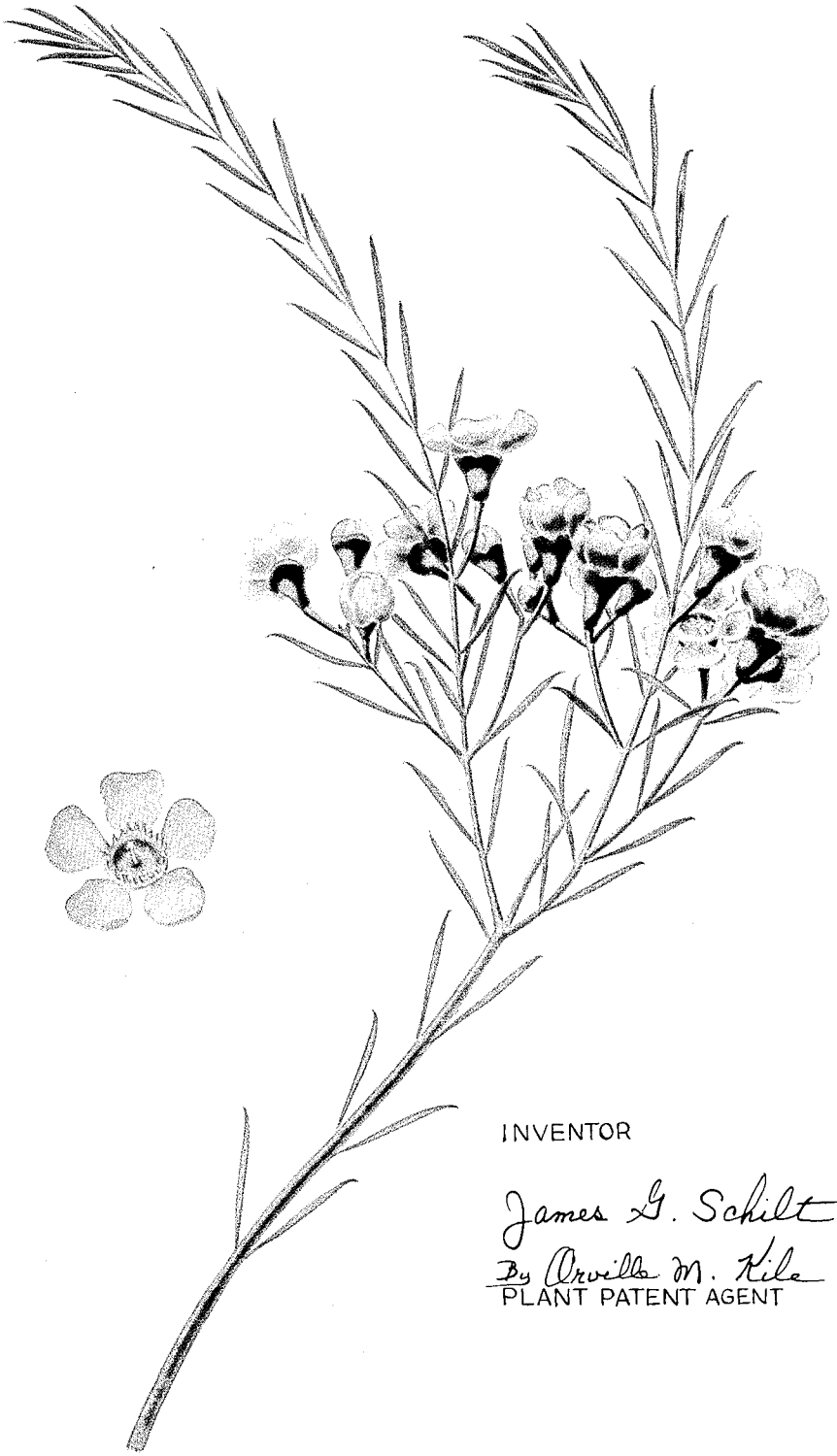
INVENTOR
James G. Schilt
By Orville M. Kile
PLANT PATENT AGENT Patented June 3, 1952

Plant Pat. 1,101

UNITED STATES PATENT OFFICE 1,101

CHAMAELAUCIUM PLANT

James G. Schilt, near Fallbrook, Calif.

Application April 30, 1951, Serial No. 223,683

1 Claim. (Cl. 47—60)

My present discovery relates to improvements in chamaelaucium plants, commonly known as the Geraldton Wax Flower.

My new variety of chamaelaucium orginated in my California gardens where it was produced by a cross between the variety C. Rubrum as the female parent and an unknown variety as the male parent. The seeds from this cross were planted and over two hundred seedlings resulted, of which one was selected as being outstanding and became the original plant of the present variety. I have reproduced the new variety in the same gardens for several years, from cuttings, and its distinguishing qualities appear to be permanent.

Outstanding among its qualities are the density of growth and large flowers of distinctly new color.

The accompanying illustrations show a spray of my new variety of chamaelaucium at the blooming season, with blossoms in various stages of opening and in approximately their true colors. It was impossible, however, for the artist to show the waxy appearance of the flowers by the use of water colors.

In the following detailed description, color plate numbers refer to Ridgway's Color Standards and Nomenclature. Where other color names are used, the ordinary dictionary meaning of the term is intended.

*The plant*

Form: Shrub, sometimes reaching the height of about 10 feet, but usually not quite so high. Much branched. Heavier and more dense in growth and foliage than other known varieties.

Maturity: A bush of this variety blooms at about 18 months from cuttings.

Blooming season: In our gardens the blooming season is from December to April, varying according to the weather.

Stems or twigs: Round and fairly smooth. Older stems are dark brown, younger ones pale brown. Young stems are slender and graceful, extending from 4 to 6 inches above the clusters of flowers. Tips of stems are often curved, the leaves or needles giving a plume-like effect above the flower clusters.

Leaves: Alternately opposite. Sesile. Needle-like and slender. Straight or gracefully curved, with slightly hooked apex. Glabrous. Length averages about 1 inch as compared to approximately ¾ inch of similar varieties grown under similar circumstances. Approximately Forest Green (Pl. XXIII). Attached to stem at more acute angle than with most varieties, causing them to lie closer to stem.

Inflorescence: The flowers are borne in corymb-like clusters proceeding from the leaf axils. They usually appear opposite and are comprised of two to four flowers each. Bracts leaflike. Pedicels slender and approximately same length and color as calyx.

Buds: Pearl-like in appearance when small, with only a little of the flower coloring in evidence. Sheathed. Open slowly, becoming large balls before breaking.

Flowers: The flower consists mainly of a deeply cupped center, surrounded by five petals attached to the edge of the cup approximately at right angles when the flower is fully open. The petals are nearly orbicular and separated from each other.

*Color.*—The petals of the opening flowers are approximately Amarinth Pink (Pl. XII), becoming Mallow Purple to Rhodamine Purple (Pl. XII) when fully mature. The center of the flower is a very deep, reddish purple, approximately Amarinth Purple (Pl. XII). This makes a much darker flower than is produced by any other variety known to me.

*Texture and appearance.*—The newly opened flower has a waxy appearance and is of substantial texture.

*Size.*—This variety also produces a larger flower than other known varieties when grown under similar conditions. The center cup of the largest flowers is approximately ¼ inch in diameter and the entire flower measures about 1 inch in diameter. This is considerably larger than flowers of other varieties known to me.

*Calyx.*—Obconical, extending from the point where the cup-center and the petals meet. Glabrous. Slightly darker than leaves. Lobes almost indistinguishable.

Reproductive organs:

*Stigma.*—Capitate, with bushy fringe of light brown.

*Stamens.*—Filaments widened at base and united to form a ring at edge of cup-center. Slightly brighter in color than cup. Anthers yellow. Staminodes toothlike and intermingled with stamens.

*Fruit.*—Borne singly in cone-shaped pod averaging about ¼ inch long and brown when ripe. Seed itself is very small, never comes loose from the pod, and is planted without removal from the pod. Percentage of fertility of seed is very small.

Having thus disclosed my discovery, I claim:

The new and improved variety of chamaelaucium plant, substantially as herein shown and described, characterized particularly in comparison with other known varieties, by its heavier plant growth; its more abundant and longer foliage, usually attached at a more acute angle; its often gracefully plumed terminal leaf branches; its larger flowers; and the darker color of its flowers.

JAMES G. SCHILT.

No references cited.